(12) United States Patent
Roose

(10) Patent No.: US 6,944,518 B2
(45) Date of Patent: Sep. 13, 2005

(54) CUSTOMIZED PROSTHESIS AND METHOD OF DESIGNING AND MANUFACTURING A CUSTOMIZED PROSTHESIS BY UTILIZING COMPUTED TOMOGRAPHY DATA

(75) Inventor: Jeffrey Roose, Milford, IN (US)

(73) Assignee: DePuy Products, Inc., Warsaw, IN (US)

(*) Notice: Subject to any disclaimer, the term of this patent is extended or adjusted under 35 U.S.C. 154(b) by 0 days.

(21) Appl. No.: 10/664,540

(22) Filed: Sep. 18, 2003

(65) Prior Publication Data

US 2005/0065628 A1 Mar. 24, 2005

(51) Int. Cl.[7] .............................................. G06F 19/00
(52) U.S. Cl. .................... 700/117; 700/118; 623/22.21; 623/22.32
(58) Field of Search .............................. 700/97, 98, 118, 700/119, 182, 117; 623/22.4, 22.31, 22.36, 22.32, 914, 16, 22, 22.21–22.28

(56) References Cited

U.S. PATENT DOCUMENTS

| 4,275,444 A | 6/1981 | Ryan |
| 4,436,684 A | 3/1984 | White |
| 4,506,393 A | 3/1985 | Murphy |
| 4,704,686 A | 11/1987 | Aldinger |
| 4,936,862 A | * 6/1990 | Walker et al. ............... 128/898 |
| 5,007,936 A | 4/1991 | Woolson |
| 5,360,446 A | 11/1994 | Kennedy |
| 5,408,409 A | 4/1995 | Glassman et al. |
| 5,735,277 A | 4/1998 | Schuster |
| 5,741,215 A | 4/1998 | D'Urso |
| 5,768,134 A | 6/1998 | Swaelens et al. |
| 5,798,924 A | 8/1998 | Eufinger et al. |
| 5,824,083 A | 10/1998 | Draenert |
| 5,824,085 A | 10/1998 | Sahay et al. |
| 5,857,853 A | 1/1999 | Van Nifterick et al. |
| 5,995,738 A | 11/1999 | DiGioia, III et al. |
| 6,002,859 A | 12/1999 | DiGioia, III et al. |
| 6,112,109 A | 8/2000 | D'Urso |
| 6,177,034 B1 | 1/2001 | Ferrone |
| 6,205,411 B1 | 3/2001 | DiGioia, III et al. |
| 6,254,639 B1 | 7/2001 | Peckitt |
| 6,327,491 B1 | 12/2001 | Franklin et al. |
| 6,458,161 B1 | * 10/2002 | Gibbs et al. ............. 623/22.32 |
| 6,464,639 B1 | 10/2002 | Kim et al. |
| 2002/0123817 A1 | 9/2002 | Clasbrummel et al. |
| 2003/0212459 A1 | * 11/2003 | Gibbs ...................... 623/22.32 |

* cited by examiner

Primary Examiner—Jayprakash N. Gandhi
Assistant Examiner—Zoila Cabrera
(74) Attorney, Agent, or Firm—Maginot, Moore & Beck (57) ABSTRACT

A method of making an acetabular prosthesis includes acquiring a first set of data defining in three dimensions at least a portion of a bone of a patient. A second set of data is computed based upon the first set of data. The prosthesis is manufactured to include an acetabular cup and an attachment part extending therefrom. The manufacturing step includes the step of forming the attachment part based on the second set of data.

31 Claims, 5 Drawing Sheets

CUSTOMIZED PROSTHESIS AND METHOD OF DESIGNING AND MANUFACTURING A CUSTOMIZED PROSTHESIS BY UTILIZING COMPUTED TOMOGRAPHY DATA

BACKGROUND OF THE INVENTION

The present invention relates to prosthetic systems for the replacement of joints or portions thereof. More particularly, the invention concerns a customized prosthesis, and a method of designing and manufacturing such a prosthesis based upon computed tomography data obtained from the patient.

For treatment of various problems with the shoulder and hip such as degenerative arthritis and trauma, one method of providing relief to a patient is to replace the articulating surfaces with an artificial or prosthetic joint. In the case of a shoulder, the humerus and glenoid articulating surfaces are replaced. In the case of a hip, the femur and acetabulum articulating surfaces can be replaced.

In such replacement, pain relief, increased motion and anatomic reconstruction of the shoulder or hip joint are goals of the orthopaedic surgeon. With multiple variations in human anatomy, prosthetic systems need to accurately replicate the joints that they replace and maintain the natural symmetry of the joints on the left and right sides of the patient's body.

A hip replacement procedure may involve a total hip replacement or a partial hip replacement. In a total hip replacement procedure, a femoral component having a head portion is utilized to replace the natural head portion of the thighbone or femur. The femoral component typically has an elongated intramedullary stem which is utilized to secure the femoral component to the patient's femur. In such a total hip replacement procedure, the natural bearing surface of the acetabulum is resurfaced or otherwise replaced with a cup-shaped acetabular component that provides a bearing surface for the head portion of the femoral component.

Acetabular cups may be secured to the acetabulum in a number of different ways. For example, an acetabular cup may be secured to the acetabulum by the use of bone cement. However, recent studies have speculated that it may be desirable to secure artificial components to natural bone structures without the use of bone cement. Hence, a number of press fit acetabular cups have been designed for cementless securement.

In either case (i.e. cemented or cementless), the acetabulum is first reamed by the surgeon in order to create a cavity into which the acetabular cup is secured by the use of a surgical tool known as a reamer. It is often difficult for the surgeon to properly match the size of the reamer to the desired acetabular cup size.

Although press fit acetabular cups have heretofore been referred to as being "generally hemispherical" in shape, such cups, in reality, are sub-hemispherical in shape. Such a configuration has a number of drawbacks associated therewith. For example, if the acetabular cup is not truly hemispherical, it may be difficult for the surgeon to ream a properly sized cavity in the acetabulum. In particular, the cutting heads of reamers are typically configured as relatively true hemispheres. Hence, when a surgeon reams the patient's acetabulum, the surgeon has to "estimate" the approximate depth of the reamed recess. More specifically, if the surgeon reams too far, the annular rim of the acetabular cup will be recessed in the reamed cavity. Conversely, if the surgeon does not ream deeply enough (i.e. "under reams"), the acetabular cup will not be fully seated in the reamed cavity of the acetabulum. In light of the fact that surgeons occasionally select a reamer that is slightly smaller in size than the acetabular cup to be implanted, under reaming may also disadvantageously lead to bone fracture of the acetabulum since excessive force is often utilized to insert the cup into the undersized (i.e. under reamed) cavity. Some of the early bone cemented cups did not suffer from this problem because they were configured more closely as "true" hemispheres. However, as indicated above, such cups undesirably required the use of bone cement during implantation thereof.

Another drawback associated with press fit acetabular cups relates to the configuration of the outer shell. In particular, in an attempt to increase retaining forces, a number of acetabular cups have been designed with a flared rim (known as dual radius or "bubble" cups) or a frusto-conically shaped annular rim portion (known as dual-geometry cups). Although the configuration of such cups may generate relatively strong retention forces at the rim portion of the cup, surface contact and therefore retention forces are relatively small at the portions of the outer shell other than the rim portion, particularly in the dome area. Moreover, such reduced surface contact at the portions of the outer shell other than the rim portion reduces bone ingrowth in such portions.

With the above-mentioned press-fit acetabular cups, a two-part reaming process is typically necessary. The two-part reaming process involves reaming of the acetabulum using a reamer of a first size, then reaming the acetabulum using a reamer of a second size. The more reaming, the more likely that a problem will occur. For example, many conventional cementless acetabular cup systems use a cup that is two millimeters larger than the last reamer size used. Inserting this size cup into the undersized reamed acetabulum to accommodate this system is sometimes difficult, particularly with resistance in the dome area of the cup, which is also larger than the last reamer size used.

In order to avoid cementing or press fitting an acetabular cup, and the associated problems described above, it is known for an acetabular cup prosthesis to include one or more flanges that are to be matingly attached to respective bones of the patient's pelvis that surround the acetabulum, i.e., the ischium, pubis and ilium. The mating surfaces of the flanges have undulations that follow the curvature of the bones to which the flanges are attached. Ideally, the flanges should have uniform thicknesses in order to maximize the flanges' strength as well as the volume of space adjacent to the flanges that is available for muscle and tissue. However, as described in more detail, below, a practical method of providing the flanges with uniform thicknesses has not thus far been achieved.

One techniques for designing the flanges involves obtaining three dimensional data defining the patient's natural hip joint via computed tomography (CT), commonly known as a CAT scan. From the CT data, a stereolithography model is made of at least a portion of the patient's natural hip joint. Clay is then pressed against the model of the hip joint in order to form a clay model of the prosthesis that is to be implanted into the patient's natural hip joint. A laser scan of the clay model is used to create an implantable embodiment of the clay model prosthesis. This prosthesis is then implanted into the patient's hip joint.

A problem with the above-described technique is that the clay models of the prosthesis can have imperfections, such as an insufficiently uniform thickness, particularly due to the model-maker's inability to see or otherwise determine the thickness of the clay at all points. When the steel prosthesis is fabricated as a replication of the clay model, its flanges also may not have sufficiently uniform thicknesses, which results in either thin areas subject to cracking or overly thick areas that deprive the muscle and tissue of needed space.

It is also known with such hip replacements to perform a CT scan on the other hip, i.e, the "good" hip, and make a stereolithographic model of the hip therefrom. From the model, the angular orientation of the acetabular cup can be measured and used to set the angular orientation of the prosthetic acetabular cup to be implanted in the "bad" hip. A first problem with this technique is the difficulty in accurately measuring the angular orientation of the acetabulum in the good hip, and replicating the angular orientation in the prosthesis to be inserted into the bad hip. A second problem is the substantial additional cost involved with making a model of the good hip.

It is also known to use computer aided design (CAD) software to design other types of prostheses based upon imported data obtained from a CT scan of a patient's body. For example, U.S. Pat. Nos. 4,436,684, 5,741,215, 5,798,924 and 6,254,639, are directed to designing an entire prosthesis based upon the CT data. However, using these prior approaches to creating a unique prosthesis design for each patient can result in unforeseeable problems and takes away the familiarity that the surgeon will likely have with standardized prosthesis designs. Thus, prosthesis designs that are entirely customized are considered sub-optimal solutions.

The use of CT data in the above patents is generally confined to the design of customized prostheses that replace a portion of bone that has been lost due to trauma or deterioration. These prior approaches are not directed to using CT data to design a prosthesis that includes an attachment part for attaching or for otherwise associating a standardized functional part with a traumatized or deteriorated bone.

Consequently, there is a need for a method of designing and manufacturing a customized prosthesis that addresses these and other drawbacks. With respect to the hip joint, there is a particular need for an acetabular prosthesis and associated method of making an acetabular prosthesis that overcomes one or more of the above-mentioned problems. More particularly, what is needed is an acetabular prosthesis and associated method of fabrication that enables the acetabular cup to be secured to the acetabulum of the innominate bone without the cup being press fit into a reamed hole in the acetabulum, and without the use of bone cement.

There is also a need for a prosthesis and associated method of fabrication that provides a flange of the prosthesis with a uniform thickness and a bone-facing surface that is complementary to a portion of the surface of the patient's bone. Again, with respect to the hip, a need remains for an acetabular prosthesis and associated method of fabrication that provides an acetabular cup with an angular orientation relative to the flanges and/or the patient's bone structure that is accurately based upon a corresponding angular orientation in the contralaterally corresponding hip.

SUMMARY OF THE INVENTION

In order to address these needs, the present invention provides a method of making a prosthesis for a joint socket in which CT data from a patient's joint is used to design the prosthesis. The CT data is downloaded into computer aided design (CAD) software in order to design at least an attachment part, and possibly a functional part, of the prosthesis. The attachment part can be used to attach or otherwise associate the functional part to the patient's bone. The functional part can have standardized dimensions, while the CAD software can design the attachment part with uniform thickness for maximum strength in a minimum of space.

CT data from the patient's other, i.e., contralaterally corresponding, "good" joint can also be acquired and used in designing the prosthesis. The angular orientation of the joint components of the good joint can be extracted from the CT data so that the CAD software can replicate the angular orientation in the design of the prosthesis. For example, the angular orientation between the functional part and the attachment part in the prosthesis, and/or between the functional part and the patient's bone structure, can be established by the CAD software based on the angular orientations in the good joint as extracted from the CT data.

In one form, the subject invention provides a method of making an acetabular prosthesis, including acquiring a first set of data defining in three dimensions at least a portion of a bone of a patient. A second set of data is computed based upon the first set of data. The prosthesis is manufactured to include an acetabular cup and an attachment part extending therefrom. The manufacturing step includes the step of forming the attachment part based on the second set of data.

In another embodiment, the subject invention provides a method of making a prosthesis for a joint socket, including acquiring a first set of data defining in three dimensions at least a portion of a bone of a patient. A second set of data based upon the first set of data is computed. The prosthesis is manufactured to include a functional part and an attachment part extending therefrom. The manufacturing step includes the step of forming the attachment part based on the second set of data.

In yet another form, the subject invention provides a method of making an acetabular prosthesis, including acquiring a first set of data defining in three dimensions at least a portion of a bone of a patient. A second set of data is computed based upon the first set of data. The prosthesis is manufactured to include an acetabular cup and an attachment part extending therefrom. The manufacturing step includes the steps of forming the attachment part based on the second set of data, forming the attachment part to include a bone-facing surface and a tissue-facing surface, and forming the tissue-facing surface to be a partial facsimile of a surface of the bone.

One aspect of the present invention contemplates an acetabular prosthesis including an acetabular cup and a flange attached to the acetabular cup. The flange is prepared by a process including the steps of acquiring a first set of data defining in three dimensions at least a portion of a bone of a patient, computing a second set of data based upon the first set of data, and manufacturing the flange based upon the second set of data.

One advantage of the present invention is that the acetabular cup does not need to be secured to the innominate bone via bone cement or press fitting. Another advantage is that the flanges of the implant can be provided with a uniform thickness and a bone-facing surface complementary to a portion of a surface of the patient's bone.

Yet another advantage is that an acetabular cup can be provided with an angular orientation relative to the flanges and/or relative to the patient's bone structure that corresponds to an angular orientation in the contralaterally corresponding hip.

A further advantage is that the prosthesis can be quickly prepared, thereby reducing the lead-time required from the request for surgery to the actual surgery. A still further advantage is that the surgical time required for implantation of the prosthesis is reduced due to the improved fit of the prosthesis on the patient's bone.

DESCRIPTION OF THE FIGURES

Corresponding reference characters indicate corresponding parts throughout the figures.

DESCRIPTION OF THE PREFERRED EMBODIMENTS

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 1:
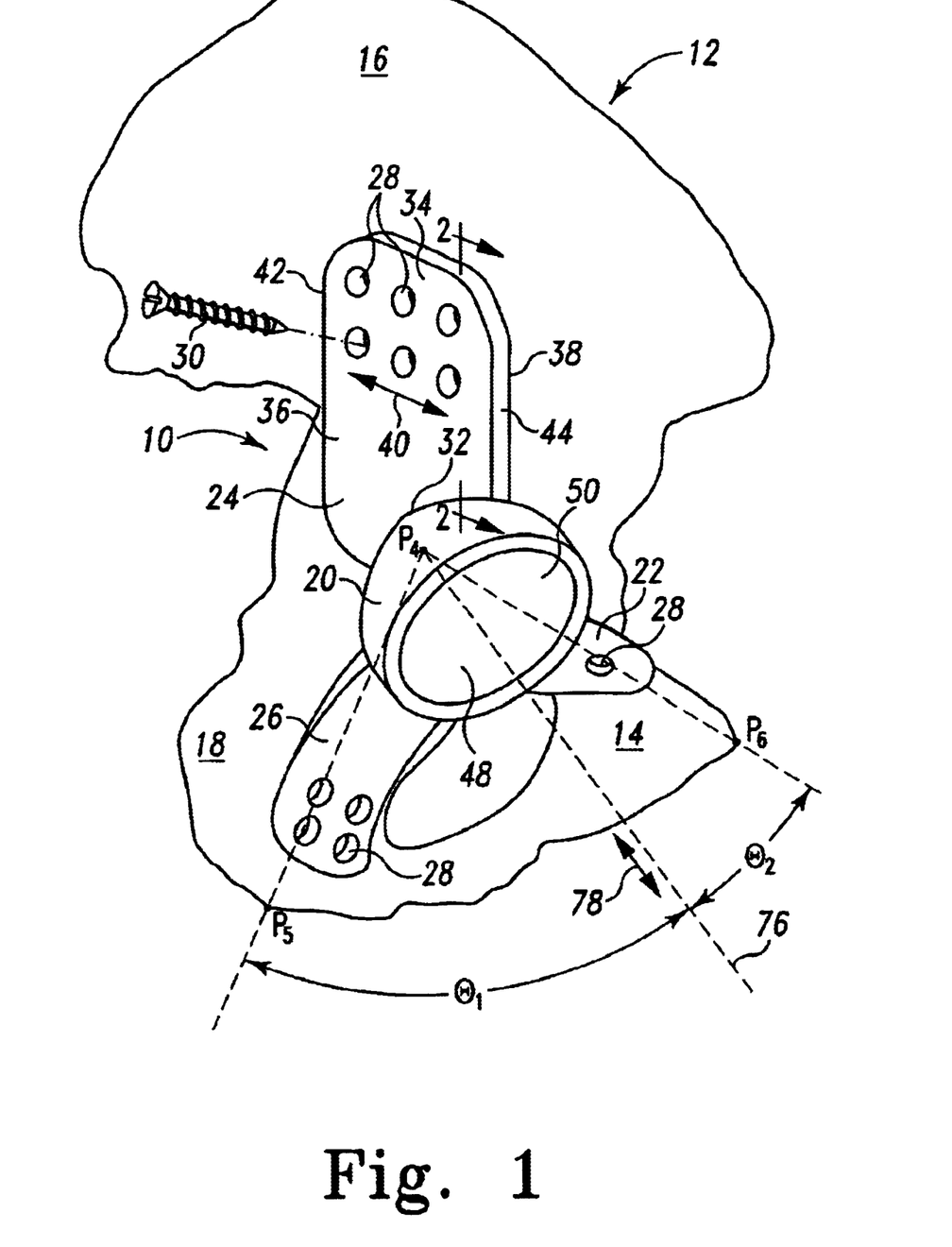
FIG. 1 is a perspective view of an acetabular replacement or prosthesis in accordance with one embodiment of the present invention, and an associated right innominate bone.

Referring to FIG. 1, there is depicted one embodiment of the subject invention comprising an acetabular prosthesis, generally designated 10, and an associated pelvic arch bone structure 12, also known as the innominate bone, including a pubis 14, ilium 16 and ischium 18. The acetabular prosthesis 10 is configured for replacement surgery in which the patient's entire hip joint is replaced. Compactness of the acetabular prosthesis 10 thus enables a minimum of the patient's bone and tissue to be removed during surgery. The acetabular prosthesis 10 and the innominate bone 12 are shown at an orientation of approximately 40° anteversion and approximately 50° abduction in FIG. 1. The depicted acetabular prosthesis 10 is for a right hip. An acetabular prosthesis for a left hip would be a mirror image of the acetabular prosthesis 10.

The acetabular prosthesis 10 includes an acetabular cup 20 and flanges 22, 24, 26 projecting from an outer surface of the cup 20. The acetabular prosthesis 10 is of monolithic construction such that the acetabular cup 20 is integrally formed with each of the flanges 22, 24 and 26.

The flanges 22, 24, 26 can be used as attachment parts to securely attach the cup 20, i.e., the functional part, to respective ones of the pubis 14, ilium 16 and ischium 18. To that end, each of the flanges 22, 24, 26 includes a possibility of one or more throughholes 28 configured to receive an anchoring element, such as a screw 30, for attaching the prosthesis 10 to the innominate bone 12.

Figure 2:
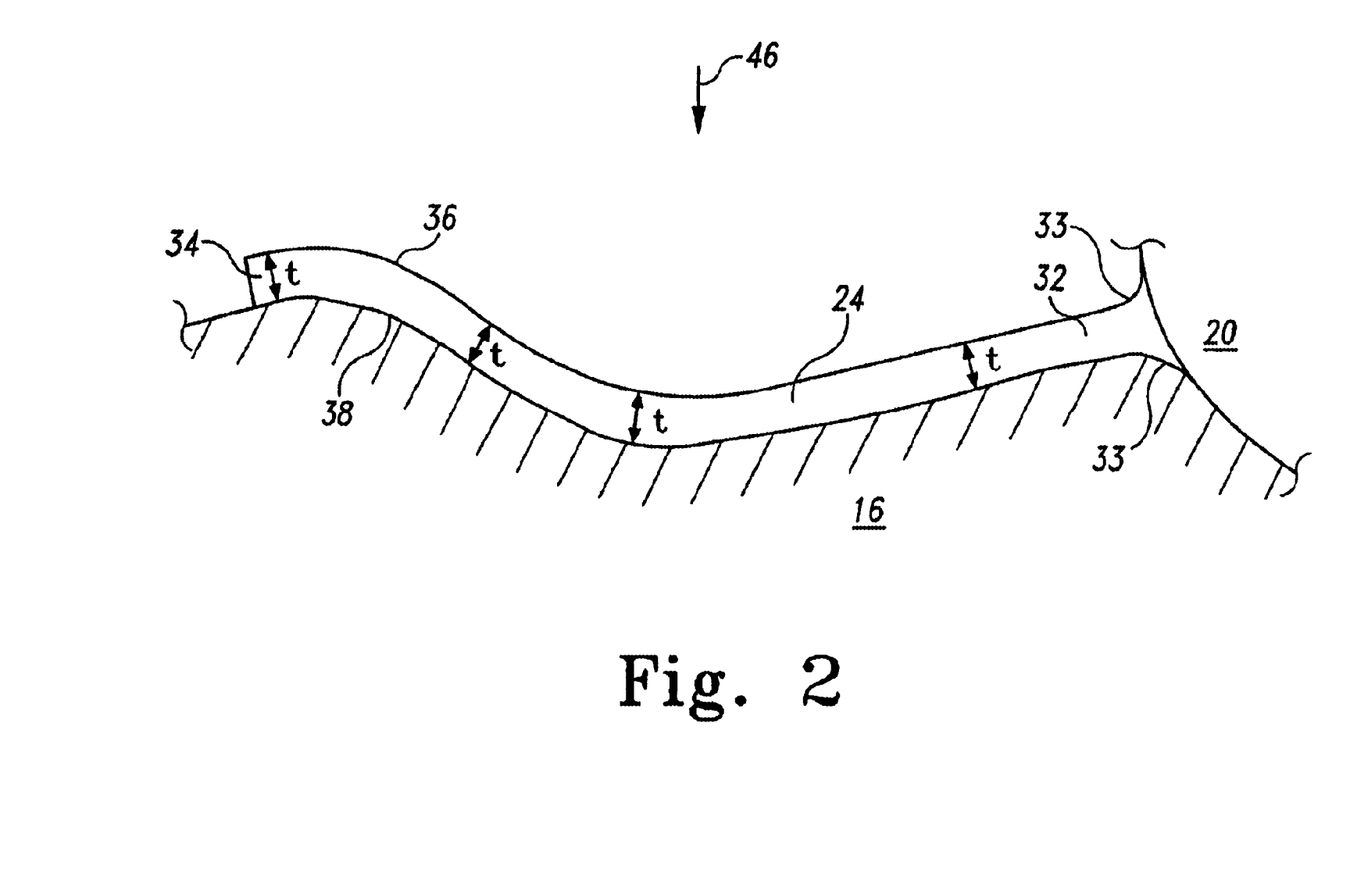
FIG. 2 is a partial, cross-sectional view of the ilium, associated flange, and the acetabular cup of the prosthesis of FIG. 1 along line 2—2 in FIG. 1.

Each of the flanges 22, 24, 26 can possess a uniform thickness extending from a cup interface portion of the flange to a free end portion of the flange. For example, FIG. 2 illustrates the uniform thickness t of the flange 24 at every point along its length from the cup interface portion 32 to the free end portion 34. As is evident from FIG. 2, the thickness t is defined to be in a direction perpendicular to both a tissue-facing surface 36 and a bone-facing surface 38 at the point of the flange 24. In a most preferred embodiment, the flange forms fillet radii 33 at the interface of the cup interface portion 32 with the cup 20 to improve the strength of that interface.

Further, each flange can possess a uniform dimension extending in any other direction across the flange. For example, the flange 24 can have a uniform width extending in a cross direction 40 (FIG. 1) between the lateral sides 42, 44 of the flange 24. It has been found that such a uniform width maximizes the structural strength of the flange within a minimum of occupied space. In a preferred embodiment, each of the flanges 22, 24, 26 has a same, equal width which is uniform across their bone-facing and tissue-facing surfaces. However, it is also understood that the respective width, or thickness, of each of the flanges 22, 24, 26 can be different.

The bone-facing surfaces of the flanges can each possess a shape that is complementary to a portion of a surface of the corresponding bone. For example, as indicated in FIG. 2, the bone-facing surface 38 of the flange 24 can possess a shape that is complementary to a portion of a surface of the ilium 16. Thus, the shape of the bone-facing surface 38 can follow the contours and undulations of the entire portion of the surface of the ilium 16 that the bone-facing surface 38 contacts.

The tissue-facing surfaces of the flanges can each be a partial facsimile of the portion of the surface of the corresponding bone. For example, as can also be seen in FIG. 2, the tissue-facing surface 36 of the flange 24 can be a partial facsimile of the associated portion of the surface of the ilium 16, albeit shifted by the thickness t of the flange away from the bone surface.

The acetabular cup 20 is generally sub-hemispherically shaped and includes a recess 48 defining by a concave articulating surface 50, as shown in FIG. 1. It is understood that the surface 50 can be integral with the cup 20 or can be part of an insert or liner that mates with the acetabular cup 20 in a known manner. The articulating surface 50 provides a bearing surface for the head of the femur similar to that of a natural hip joint. The articulating surface 50 provides the patient with approximately the same range of movement as that of a natural hip. When the prosthesis 10 is implanted into a patient, the acetabular cup 20 can be positioned approximately in the same position as the patient's former acetabulum. Thus, it may be necessary to at least partially remove any remaining portion of the acetabulum at the affected joint in order to accommodate the prosthetic cup 20.

Figure 3:
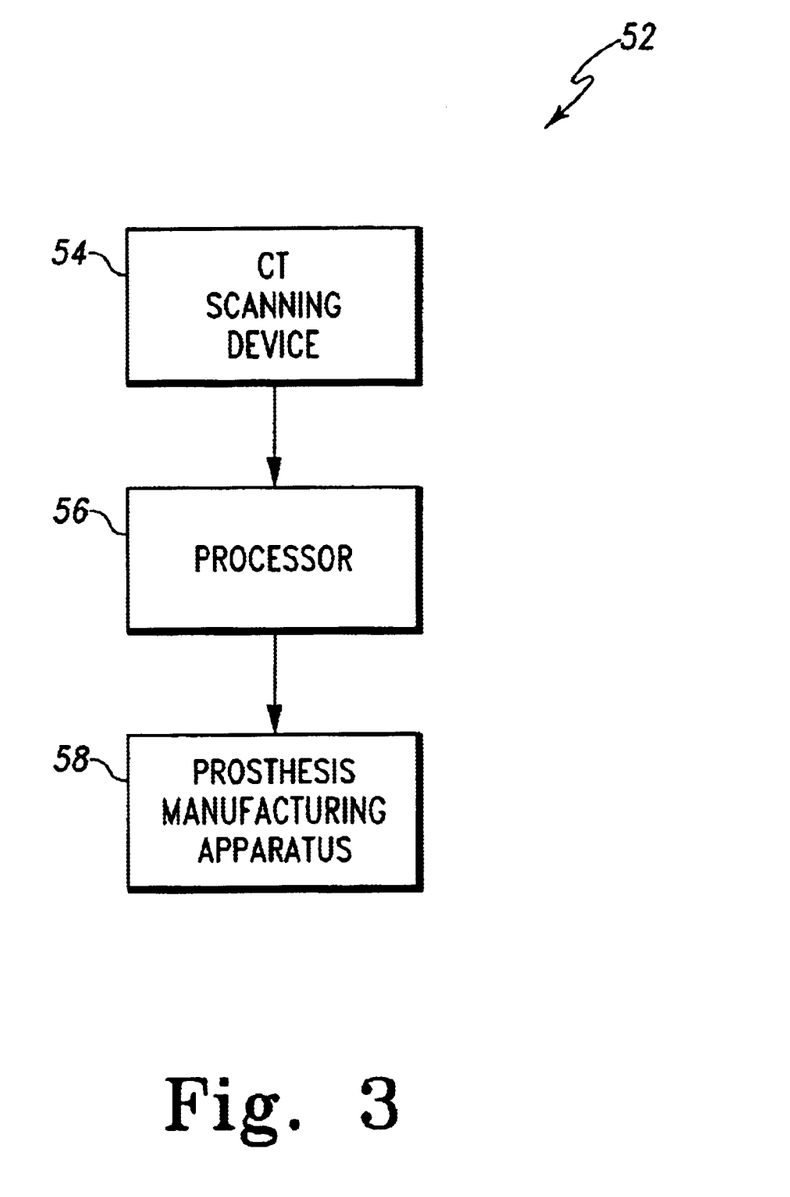
FIG. 3 is a block diagram of one embodiment of an arrangement for designing and manufacturing the prosthesis of FIG. 1.

In accordance with the present invention, the prosthesis 10 can be designed and manufactured by the general process of: performing a CT scan of the patent's innominate bone; acquiring surface data from the scan data, wherein the surface data defines in three dimensions the patient's bone surface; feeding the surface data into CAD software; and manufacturing the prosthesis according to a design produced by the CAD software. FIG. 3 illustrates one preferred embodiment of an arrangement 52 for performing this general process. The arrangement 52 includes a CT scanning device 54, a processor 56 and a prosthesis manufacturing apparatus 58.

The CT scanning device 54 can be any device capable of collecting data that defines at least the relevant part of the patient's innominate bone, namely the portion of the innominate bone that is engaged by the prosthesis 10. As is well known in the art, such a CT scanner can collect a series of two-dimensional data slices from various scanning orientations, and three-dimensional scan data can be generated from the two-dimensional data slices. This function of generating the three-dimensional scan data from the two-dimensional data slices can be performed either within the CT scanning device 54 or within the processor 56.

The three-dimensional scan data may define the entire innominate bone, and may include certain thickness information that is not needed in order to design the prosthesis 10. The three-dimensional scan data may also include data defining other bone structures or other body parts that also are irrelevant to the design of the prosthesis 10. The processor 56 can include surfacing software that extracts a set of three-dimensional surface data defining at least the relevant part of the surface of the patient's innominate bone from the three-dimensional scan data.

The processor 56 can also include CAD software that receives as an input the three-dimensional surface data and outputs a design of the prosthesis 10 that is based on the three-dimensional surface data. Alternatively, the CAD software can be stored in the prosthesis manufacturing apparatus 58. The prosthesis design produced by the CAD software can be in the form of three-dimensional design data that defines the prosthesis.

In a preferred embodiment, the prosthesis design produced by the CAD software can include a standardized design for the acetabular cup 20, i.e., the acetabular cup design can have standardized dimensions familiar to the surgeon. The prosthesis design can also include customized flange designs, wherein the bone-facing surfaces of the flanges are complementary to the surfaces of the associated bones, and the flanges have uniform thicknesses, as described in more detail above in connection with FIGS. 1 and 2.

The prosthesis manufacturing apparatus 58 can be any computer controlled manufacturing unit that is capable of manufacturing a monolithic prosthesis that conforms to the prosthesis design produced by the CAD software. In one embodiment, the apparatus 58 can be in the form of a CNC machine.

The processor 56 can share a housing with either the CT scanning device 54 or the prosthesis manufacturing apparatus 58. Alternatively, the processor 56 can be a stand-alone unit that is disposed outside the housings of the CT scanning device 54 and the prosthesis manufacturing apparatus 58.

Figure 4:
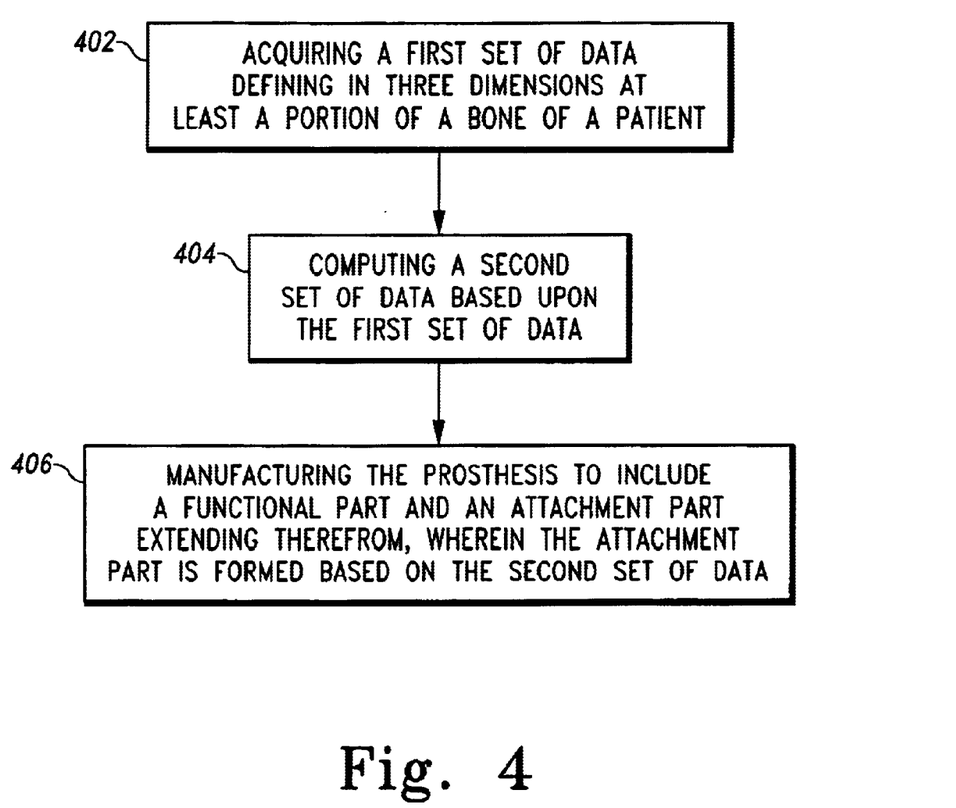
FIG. 4 is a flow chart of one embodiment of a method of making a prosthesis for a joint socket according to the present invention.

A preferred embodiment of a method for making a prosthesis for a joint socket according to the present invention will be described herein in association with FIG. 4. In a first step 402, a first set of data is acquired wherein the data defines in three dimensions at least a portion of a bone of a patient. For example, in the case of the acetabular prosthesis 10, the CT scanning device 54 can collect a series of two-dimensional data slices which collectively define at least the relevant portion of the innominate bone 12 in three dimensions. From this data, the CT scanning device 54 itself or the processor 56 can extract three-dimensional surface data that defines at least the portion of the surface of the innominate bone 12 that the prosthesis 10 is to engage.

In a next step 404, a second set of data is computed based upon the first set of data. Continuing the example discussed above in connection with step 402, the CAD software can compute a second set of three-dimensional design data that defines at least the flanges 22, 24, 26 of the prosthesis. Data that defines an acetabular cup 20 of standardized dimensions may be imported into the CAD software and computationally merged with the flange design data within the CAD software. Alternatively, a customized design of the acetabular cup 20 may also be computed within the CAD software. The computation of at least the flange-related portion, and possibly the acetabular cup-related portion, of the prosthesis design data can be based upon the three-dimensional surface data that defines at least the relevant portion of the surface of the innominate bone 12.

In a final step 406, the prosthesis is manufactured to include a functional part and an attachment part extending therefrom, wherein the attachment part is formed based on the second set of data. Continuing the above example, the prosthesis manufacturing apparatus 58 can be used to manufacture the prosthesis 10 to include a functional part in the form of an acetabular cup 20 and attachment parts in the form of flanges 22, 24, 26. The flanges can be formed by the apparatus 58 based upon the three-dimensional design data computed by the CAD software to define the flanges 22, 24, 26. The apparatus 58 can form the acetabular cup portion of the prosthesis based on either standardized design data imported into the CAD software or three-dimensional design data computed by the CAD software to define the acetabular cup 20.

In a preferred embodiment, step 406 can include forming the attachment part to include a bone-facing surface and a tissue-facing surface. In the above example, the manufacturing apparatus 58 forms the flange 24 to include a bone-facing surface 38 and a tissue-facing surface 36. Step 406 can also include forming the tissue-facing surface to be a partial facsimile of a surface of the patient's bone. In the specific example, the tissue-facing surface 36 can be formed to be a partial facsimile of the portion of the surface of the ilium 16 with which the tissue-facing surface 36 is associated.

In the embodiments discussed thus far in connection with FIGS. 1–4, the design of the prosthesis 10 has been described as being based upon CT data acquired in a scan of only the hip into which the prosthesis 10 is to be inserted. However, in a further embodiment discussed herein in connection with FIG. 5, the design of the prosthesis 10 can be based upon CT data acquired in scans of not only the hip into which the prosthesis 10 is to be inserted, but also the contralaterally corresponding hip, i.e., the hip that does not require surgical repair.

Figure 5:
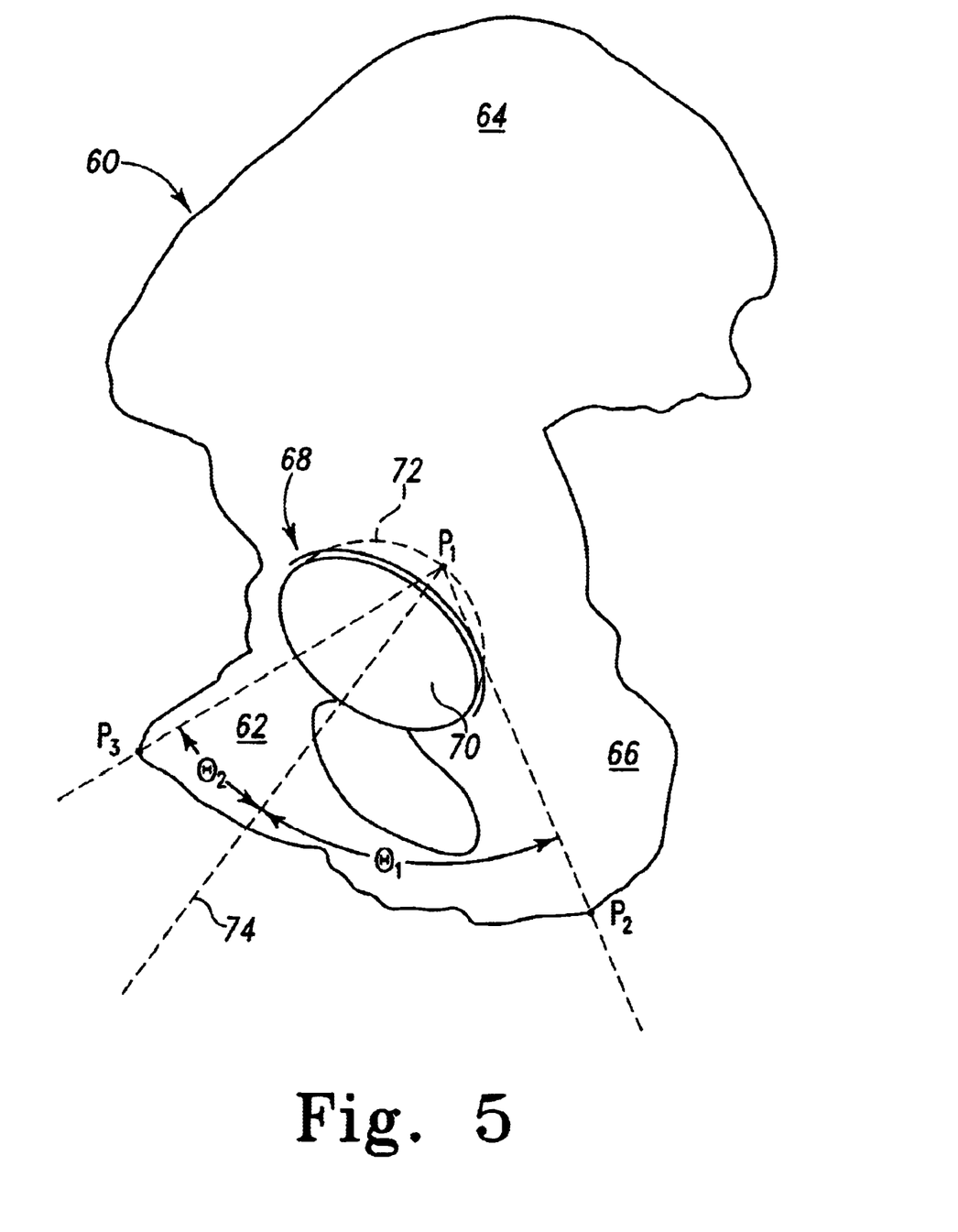
FIG. 5 is a perspective view of the left innominate bone contralaterally corresponding to the right innominate bone of FIG. 1.

More particularly, an angular orientation of the acetabular cup 20 relative to the innominate bone 12 and/or relative to at least one of the flanges 22, 24, 26 can be arranged based at least partially on data acquired in a CT scan of the contralaterally corresponding hip. It may be desirable to achieve symmetry in the patient's hips such that an angular orientation of the acetabular cup 20 is approximately equal to the angular orientation of the acetabulum in the patient's other, "good" hip.

The prosthesis 10 is shown in FIG. 1 to be applied to the patient's right hip, or, more specifically, to the patient's right innominate bone 12. FIG. 5 illustrates the patient's left innominate bone 60 which contralaterally corresponds to the right innominate bone 12. The left innominate bone 60 includes a pubis 62, an ilium 64, an ischium 66 and an acetabulum 68. In similar fashion to the acetabular cup 20, the acetabulum 68 includes a recess 70 defined by an articulating surface 72.

From the CT scan data, the locations of all of the points on the surface of the innominate bone 60 can be determined.

An angular orientation of a central axis 74 of the acetabulum 68 can be determined from the CT scan data. The central axis 74 can be used within the CAD software to define an angular orientation of the acetabulum 68. More particularly, the angular orientation of the acetabulum 68 can be defined with reference to the central axis 74 relative to any convenient bony landmarks on the innominate bone 60 or on other bone structure.

In the example shown in FIG. 5, a reference point $P_1$ is defined at the intersection of the central axis 74 and the articulating surface 72. A second reference point $P_2$ is defined at a first bony landmark in the form of an outermost point on the ischium 66. A third reference point $P_3$ is defined at a second bony landmark in the form of an outermost point on the pubis 62. From the CT scan data, a first angle $\theta_1$ between the axis 74 and a line intersecting points $P_1$, $P_2$ can be calculated by the CAD software. A second angle $\theta_2$ between the axis 74 and a line intersecting points $P_1$, $P_3$ can also be calculated. The angular orientation of the central axis 74, and thus of the acetabulum 68 itself, can be defined by the two angles $\theta_1$, and $\theta_2$. It is to be understood that the axis 74, the line intersecting points $P_1$, $P_2$, and the line intersecting points $P_1$, $P_3$ are not likely to be coplanar, although they may appear to be coplanar in the two-dimensional illustration of FIG. 5.

The CAD software can use the CT data acquired in a scan of the left hip to replicate at least some of the left hip bone structure, or create a mirror image of at least some of the left hip bone structure, in the design of the prosthesis 10 to be inserted into the right hip. More particularly, in order to make use of the CT data from the left hip, the CAD software can determine the locations of corresponding reference points $P_5$ and $P_6$ in the right hip, which reference points are shown in FIG. 1. The CAD software can determine the locations of the reference points $P_5$ and $P_6$ from the data acquired in the CT scan of the right innominate bone 12. Using data acquired in scans of both the right and left hips, the CAD software can compute a design of the prosthesis 10 such that the angles $\theta_1$ and $\theta_2$ from the left hip are replicated in the right hip. Specifically, the prosthesis 10 can be designed with angular orientations between the cup 20 and the flanges 22, 24, 26 such that, when the flanges are matingly engaged with the innominate bone 12, the angles $\theta_1$ and $\theta_2$ from the left hip are mirrored to the right hip to receive the prosthesis.

A reference point $P_4$ is defined as the point of intersection between a central axis 76 of the cup 20 and the articulating surface 50. The CAD software can design the prosthesis 10 such that an angle between the axis 76 and a line intersecting points $P_4$, $P_5$ is equal to $\theta_1$, i.e., equal to the corresponding angle in the left hip. The prosthesis 10 can also be designed such that an angle between the axis 76 and a line intersecting points $P_4$, $P_6$ is equal to $\theta_2$, i.e., equal to the corresponding angle in the left hip.

The orientations of the flanges 22, 24, 26 can be dictated by the orientations and/or surface shapes of the associated bones. The CAD software can arrange the angular orientation of the cup 20 relative to the flanges 22, 24, 26 such that the angles $\theta_1$ and $\theta_2$ are replicated when the flanges 22, 24, 26 are matingly engaged with their associated bones. In order to achieve this orientation, the CAD software can position the cup 20 in the prosthesis design such that the angles $\theta_1$ and $\theta_2$ are replicated and such that the cup 20 is positioned to be attached to each of the flanges 22, 24, 26. Thus, the angular orientation of the cup 20 relative to the bony landmarks $P_5$, $P_6$ and relative to the flanges 22, 24, 26 is arranged by the CAD software based on the CT data acquired in connection with the left innominate bone 60.

It should be understood that the CAD software can also establish the position, or depth, of the cup 20 along the axis 76, i.e., in the directions indicated by double arrow 78. This position of the cup 20 along the axis 76 may also be established by the CAD software based upon the CT data acquired in connection with the left innominate bone 60.

Alternatively, the geometry obtained for the "good" hip can be mirrored for the affected hip joint. A best fit approximation of this mirrored image can be generated for the affected joint. The CAD software can then fit a sphere to the mirrored acetabulum, which can then be used to define the center of the acetabular cup to which the flanges will be attached. The orientation of the acetabular rim can then be extracted from the mirrored image data and used to dictate the orientation and location of the face of the acetabular cup.

The embodiment discussed above in connection with FIG. 5 has been described as being intended to achieve symmetry between the patient's left and right hips. However, even if it is not desirable under certain circumstances to achieve symmetry in the patient's contralaterally corresponding hips, a CT scan of the other, "good" hip may provide data that is useful in arranging the acetabular cup 20 at an orientation that is beneficial.

It is, of course, possible to establish the angular orientations of the acetabulum 68 and/or the acetabular cup 20 relative to landmarks, bony or otherwise, that are different than the bony landmarks described herein. For example, it may be desirable to establish the angular orientations of the acetabulum 68 and/or the acetabular cup 20 relative to the head of the femur with which they are associated.

The acetabular prosthesis 10 can be formed of a conventional bio-compatible metal or a suitably strong material such as a titanium alloy or a cobalt-chromium alloy. The acetabular prosthesis 10 can be porous coated depending upon the preferred application. The acetabular cup and the flanges can be provided in various sizes and shapes to accommodate various patient hip sizes and shapes.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected. For instance, while the present invention is shown and described with respect to a hip joint, it should be understood that the principles of the subject invention as described herein are applicable to prostheses for joints other than the hip, particularly for articulating surface joints similar to the hip.

What is claimed is:

1. A method of making an acetabular prosthesis comprising the steps of:

acquiring a first set of data defining in three dimensions at least a portion of a bone of a patient;

computing a second set of data based upon the first set of data; and manufacturing said prosthesis to include an acetabular cup and an attachment part extending therefrom configured to attach the acetabular cup to bone surrounding the acetabulum of a patient, wherein said manufacturing step includes the step of forming said attachment part based on the second set of data.

2. The method of claim 1, wherein said second set of data defines in three dimensions said attachment part.

3. The method of claim 1, wherein:
   said attachment part comprises a flange extending from said acetabular cup, and
   said flange has defined therein a number of throughholes configured to receive an anchoring element.

4. The method of claim 1, wherein said manufacturing step further includes the steps of:
   forming said attachment part to include a bone-facing surface and a tissue-facing surface, and
   forming said tissue-facing surface to be a partial facsimile of a surface of said bone.

5. The method of claim 4, wherein said manufacturing step further includes the step of forming said bone-facing surface to possess a shape complementary to a portion of the surface of said bone.

6. The method of claim 1, wherein:
   said attachment part possesses a cup interface end portion and a free end portion, and
   said forming step includes forming said attachment part with a uniform thickness extending from said cup interface end portion to said free end portion.

7. The method of claim 1, wherein said manufacturing step further includes the steps of
   forming said attachment part to include a bone-facing surface and a tissue-facing surface, and
   forming said bone-facing surface to possess a shape complementary to a portion of a surface of said bone.

8. The method of claim 1, further comprising the step of acquiring a third set of data defining in three dimensions other bone structure of the patient, at least some of said other bone structure contralaterally corresponding to said bone of the patient, wherein:
   said manufacturing step includes the step of arranging an angular orientation of said acetabular cup relative to at least one of said attachment part and the bone of the patient based on said third set of data.

9. A method of making a prosthesis for a joint socket comprising the steps of:
   acquiring a first set of data defining in three dimensions at least a portion of a bone of a patient;
   computing a second set of data based upon the first set of data; and
   manufacturing said prosthesis to include a functional part and an attachment part extending therefrom configured to attach the functional part to the bone surrounding the joint socket,
   wherein said manufacturing step includes the step of forming said attachment part based on the second set of data.

10. The method of claim 9, wherein said second set of data defines in three dimensions said attachment part.

11. The method of claim 9, wherein:
    said attachment part comprises a flange extending from said functional part, and
    said flange has defined therein a number of throughholes configured to receive an anchoring element.

12. The method of claim 9, wherein said manufacturing step further includes the steps of:
    forming said attachment part to include a bone-facing surface and a tissue-facing surface, and
    forming said tissue-facing surface to be a partial facsimile of a surface of said bone.

13. The method of claim 12, wherein said manufacturing step further includes the step of forming said bone-facing surface to possess a shape complementary to a portion of the surface of said bone.

14. The method of claim 13, wherein:
    said attachment part possesses a cup interface end portion and a free end portion, and
    said attachment part possesses a uniform thickness extending from said cup interface end portion to said free end portion.

15. The method of claim 9, wherein said manufacturing step further includes the steps of:
    forming said attachment part to include a bone-facing surface and a tissue-facing surface, and
    forming said bone-facing surface to possess a shape complementary to a portion of a surface of said bone.

16. The method of claim 9, further comprising the step of acquiring a third set of data defining in three dimensions other bone structure of the patient, at least some of said other bone structure contralaterally corresponding to said bone of the patient, wherein:
    said manufacturing step includes the step of arranging an angular orientation of said functional part relative to at least one of said attachment part and the bone of the patient based on said third set of data.

17. The method of claim 9, wherein said manufacturing step includes manufacturing said functional part from predetermined data.

18. A method of making an acetabular prosthesis comprising the steps of:
    acquiring a first set of data defining in three dimensions at least a portion of a bone of a patient;
    computing a second set of data based upon the first set of data;
    manufacturing said prosthesis to include an acetabular cup and an attachment part extending therefrom configured to attach the acetabular cup to bone surrounding the acetabulum of a patient, wherein said manufacturing step includes the steps of:
    forming said attachment part based on the second set of data,
    forming said attachment part to include a bone-facing surface and a tissue-facing surface, and
    forming said tissue-facing surface to be a partial facsimile of a surface of said bone.

19. The method of claim 18, wherein said second set of data defines in three dimensions said attachment part.

20. The method of claim 18, wherein:
    said attachment part comprises a flange extending from said acetabular cup, and
    said flange has defined therein a number of throughholes configured to receive an anchoring element.

21. The method of claim 18, further comprising the step of acquiring a third set of data defining in three dimensions other bone structure of the patient, at least some of said other bone structure contralaterally corresponding to said bone of the patient, wherein:
    said manufacturing step includes the step of arranging an angular orientation of said acetabular cup relative to at least one of said attachment part and the bone of the patient based on said third set of data.

22. An acetabular prosthesis, comprising:
    an acetabular cup; and
    a flange attached to said acetabular cup and configured to attach the acetabular cup to bone surrounding the acetabulum of a patient, said flange is prepared by a process including the steps of:

acquiring a first set of data defining in three dimensions at least a portion of a bone of a patient;

computing a second set of data based upon the first set of data; and manufacturing said flange based upon the second set of data.

23. The prosthesis of claim 22, wherein said second set of data defines in three dimensions said flange.

24. The prosthesis of claim 22, wherein said flange has defined therein a number of throughholes configured to receive an anchoring element.

25. The prosthesis of claim 22, wherein said manufacturing step further includes the steps of:

forming said flange to include a bone-facing surface and a tissue-facing surface, and forming said tissue-facing surface to be a partial facsimile of a surface of said bone.

26. The prosthesis of claim 25, wherein said manufacturing step further includes the step of forming said bone-facing surface to possess a shape complementary to a portion of the surface of said bone.

27. The prosthesis of claim 22, wherein:

said flange possesses a cup interface end portion and a free end portion, and said flange possesses a uniform thickness extending from said cup interface end portion to said free end portion.

28. The prosthesis of claim 22, wherein said manufacturing step further includes the steps of:

forming said flange to include a bone-facing surface and a tissue-facing surface, and forming said bone-facing surface to possess a shape complementary to a portion of a surface of said bone.

29. The prosthesis of claim 22, wherein the process further comprises the step of acquiring a third set of data defining in three dimensions other bone structure of the patient, at least some of said other bone structure contralaterally corresponding to said bone of the patient, and wherein said manufacturing step includes the step of arranging an angular orientation of said acetabular cup relative to at least one of said flange and the bone of the patient based on said third set of data.

30. A method of making an acetabular prosthesis comprising the steps of:

acquiring a first set of data defining in three dimensions at least a portion of a bone of a patient;

computing a second set of data based upon the first set of data; and manufacturing said prosthesis to include an integral component including an acetabular cup and an attachment part extending therefrom, wherein said manufacturing step includes the step of forming said attachment part based on the second set of data.

31. The method of claim 30 wherein the integral component of the manufactured prosthesis is monolithic.

* * * * *